(12) United States Patent
Li et al.

(10) Patent No.: US 11,313,775 B2
(45) Date of Patent: Apr. 26, 2022

(54) DEVICE AND METHOD FOR EVALUATING FRACTURE INITIATION AND PROPAGATION, AND STRESS SENSITIVITY OF PROPPED FRACTURE

(71) Applicant: Southwest Petroleum University, Chengdu (CN)

(72) Inventors: Yongming Li, Chengdu (CN); Bo Chen, Chengdu (CN); Zixi Guo, Chengdu (CN)

(73) Assignee: Southwest Petroleum University, Chengdu (CN)

( * ) Notice: Subject to any disclaimer, the term of this patent is extended or adjusted under 35 U.S.C. 154(b) by 0 days.

(21) Appl. No.: 16/879,156

(22) Filed: May 20, 2020

(65) Prior Publication Data
US 2021/0088429 A1     Mar. 25, 2021

(30) Foreign Application Priority Data

Oct. 9, 2019   (CN) .......................... 2019109548531

(51) Int. Cl.
| | |
|---|---|
| *G01N 3/10* | (2006.01) |
| *G01N 3/06* | (2006.01) |
| *G01N 33/24* | (2006.01) |

(52) U.S. Cl.
CPC .............. *G01N 3/10* (2013.01); *G01N 3/062* (2013.01); *G01N 3/068* (2013.01); *G01N 33/24* (2013.01); *G01N 2203/0067* (2013.01); *G01N 2203/0256* (2013.01)

(58) Field of Classification Search
CPC .......... G01N 3/10; G01N 3/062; G01N 3/068; G01N 33/24; G01N 2203/0067; G01N 2203/0256
See application file for complete search history.

(56) References Cited

U.S. PATENT DOCUMENTS

| | | | | |
|---|---|---|---|---|
| 4,635,719 A | * | 1/1987 | Zoback | ................. E21B 49/006 166/250.1 |
| 4,733,567 A | * | 3/1988 | Serata | ...................... G01V 1/46 73/784 |
| 5,963,508 A | * | 10/1999 | Withers | ................. G01V 1/008 166/250.1 |
| 2006/0219402 A1 | * | 10/2006 | Lecampion | ............. E21B 47/02 166/250.1 |
| 2012/0000662 A1 | * | 1/2012 | Liskowitz | ............... E21B 43/26 166/308.1 |
| 2014/0372089 A1 | * | 12/2014 | Weng | ..................... E21B 43/26 703/2 |
| 2016/0108705 A1 | * | 4/2016 | Maxwell | ............... E21B 43/267 166/250.1 |

* cited by examiner

*Primary Examiner* — Max H Noori
(74) *Attorney, Agent, or Firm* — Pearne & Gordon LLP (57) ABSTRACT

A device and method for evaluating fracture initiation and propagation, and a stress sensitivity of a propped fracture is provided. The device includes a core part, a confining pressure loading part, a fracturing fluid pumping part, a stress sensitivity testing part and a fracture monitoring part. The method evaluates fracture initiation and propagation, and a stress sensitivity of a propped fracture using the above device and is reliable and simple to operate and guides optimization of construction parameters of hydraulic fracturing, thus achieving improvement in productivity of an oil and gas well.

8 Claims, 3 Drawing Sheets

DEVICE AND METHOD FOR EVALUATING FRACTURE INITIATION AND PROPAGATION, AND STRESS SENSITIVITY OF PROPPED FRACTURE

CROSS-REFERENCE TO RELATED APPLICATION

This application claims priority under 35 U.S.C. § 119 to Chinese Patent Application No. 2019109548531, filed Sep. 24, 2019, which is incorporated herein by reference in its entirety.

FIELD OF THE INVENTION

The present invention belongs to the field of oil and gas field development, and more particularly, relates to a device and method for integrally evaluating fracture initiation and propagation, and a stress sensitivity of a propped fracture.

BACKGROUND

A hydraulic fracturing technology always plays a critical role during exploration and development of unconventional oil and gas resources, and due to generally poor porosity, permeability and other physical properties of unconventional reservoirs, certain stimulation measures may be performed on most producing wells before putting into production. The hydraulic fracturing technology is commonly used to improve a single well productivity, a core of stimulation by the hydraulic fracturing technology is to provide a high-speed channel for oil and gas to flow into a wellbore and enhance a connectivity between the wellbore and the reservoir through a flow conductivity of a hydraulic fracture.

Initiation and propagation paths, and a stress sensitivity of the hydraulic fracture all directly affect a reconstruction effect of hydraulic fracturing. At present, numerical simulation and an indoor core fracturing simulation test are mainly used to study hydraulic fracture initiation and propagation, while testing on a variation of a permeability of a small cylindrical core (with a diameter generally less than 10 cm) with a stress is mainly used to study a fracture stress sensitivity, and these methods have certain deficiencies and limitations.

(1) The numerical simulation is able to well simulate and intuitively display a complete process of the hydraulic fracture initiation and propagation, but is greatly affected by a boundary condition, an initial condition and parameter setting, and coupled with many overly idealized assumptions in the simulation, the numerical simulation is unable to truly reflect fracture initiation and propagation states in a reservoir rock which is an inhomogeneous and highly random porous medium.

(2) A large-size cubic core is used and true triaxial confining pressures are applied in the indoor core fracturing simulation test, which is able to well simulate the hydraulic fracture propagation state of the core under an underground stress, while it is an important means to represent a hydraulic fracturing effect and optimize construction parameters by monitoring the fracture propagation path and the variation of the permeability before and after fracturing in a hydraulic fracturing test.

(3) The fracture stress sensitivity test has the following problems: sizes of the core and the fracture are too small; artificial splitting is generally used to produce the fracture, which is not real hydraulic fracture; a proppant in the fracture is added in advance and is not carried in by a fracturing fluid; only one-way seepage is able to be simulated, and seepage around the wellbore is unable to be simulated; and an entire cylindrical surface of the core is wrapped and pressurized to apply a confining pressure instead of realizing true triaxial pressurization, thus having a great limitation.

SUMMARY OF THE INVENTION

The present invention provides a device for evaluating fracture initiation and propagation, and a stress sensitivity of a propped fracture, the device simulates fracturing and propping processes of a hydraulic fracture by applying triaxial confining pressures to a large-sized core and injecting liquid carbon dioxide or a fracturing fluid into the core, monitors a propagation state of the hydraulic fracture through an acoustic emission device and high-speed cameras, monitors a change of a permeability of the core before and after fracturing and under different confining pressures through a gas flow or a liquid flow, and evaluates a fracturing reconstruction effect and a stress sensitivity of a propped fracture.

The present invention also provides a method for evaluating fracture initiation and propagation, and a stress sensitivity of a propped fracture using the above device, the method is reliable in principle and simple to operate, and is able to better guide application of hydraulic fracturing and optimization of construction parameters, thus achieving the purpose of improving a productivity of an oil and gas well.

The invention relates to a device and method for evaluating fracture initiation and propagation, and a stress sensitivity of a propped fracture. The device includes a core part, a confining pressure loading part, a fracturing fluid pumping part, a stress sensitivity testing part and a fracture monitoring part. The method includes: step 1: setting X-axis, Y-axis and Z-axis pressures, and applying triaxial loads to a core; step 2: calculating a uniaxial permeability or an overall triaxial permeability of the core flowing from a wellbore to a reservoir or from the reservoir to the wellbore; step 3: adding a fracturing fluid into a first intermediate container as a prepad fluid, and adding the fracturing fluid and a proppant into a second intermediate container and using the mixture as a sand-carrying fluid; step 4: injecting the prepad fluid into the core, and injecting the sand-carrying fluid into the core after the core is fractured; and step 5: injecting water or gas into the wellbore or triaxial seepage plates, and calculating the uniaxial permeability or the overall triaxial permeability of the core flowing from the wellbore to the reservoir or from the reservoir to the wellbore after fracturing. The invention is able to guide optimization of construction parameters of hydraulic fracturing and effectively improve a productivity of an oil and gas well.

In order to achieve the above technical objects, the following technical solutions are used in the present invention.

The present invention has the technical ideas as follows: triaxial confining pressures are applied to a cubic core through hydraulic pumps to stimulate a three-dimensional crustal stress of a reservoir, and liquid carbon dioxide, an acid fluid, a fracturing fluid or a sand-carrying fluid is injected into an artificial wellbore in the core through a constant-speed and constant-pressure pump, so as to fracture and prop a hydraulic fracture; fracture initiation and propagation in the core are monitored through an acoustic emission device and high-speed cameras during fracturing, and the core is split after fracturing for verification; and overall triaxial permeabilities or uniaxial permeabilities of the core with a propped fracture under different confining pressures are tested by applying different triaxial confining pressures to the core fractured and injected with a proppant, so as to evaluate a stress sensitivity of the propped fracture thereof.

The device for evaluating the fracture initiation and propagation, and the stress sensitivity of the propped fracture includes a core part, a confining pressure loading part, a fracturing fluid pumping part, a stress sensitivity testing part and a fracture monitoring part:

the core part is composed of a wellbore casing, a wellbore sealant, an uncased wellbore, a core supporting plate and a core: the wellbore casing is fixed in a borehole in the core through the wellbore sealant, an uncased part is reserved at a lower end of the borehole as a fracture initiation part, the core is located on the core supporting plate, and the core is put into a confining pressure base through the core supporting plate and a matched bolt.

The confining pressure loading part is composed of X-axis, Y-axis and Z-axis hydraulic pumps, an oil tank, a confining pressure cover plate, the confining pressure base, an X-axis backing plate, an X-axis oil cylinder, a Y-axis backing plate, a Y-axis oil cylinder, a Z-axis upper backing plate, a Z-axis lower backing plate and a Z-axis oil cylinder. The hydraulic pumps of all axes are connected with the oil cylinders of all axes, the X-axis and Y-axis oil cylinders are connected with the X-axis and Y-axis backing plates, the Z-axis oil cylinder is connected with the Z-axis lower backing plate, and the core is located in the backing plates of all axes.

The fracturing fluid pumping part is composed of a $CO_2$ check valve, a $CO_2$ intermediate container, a low-temperature bath, a $CO_2$ pressure regulating valve, a $CO_2$ gas cylinder, a constant-speed and constant-pressure pump, a first water storage tank, a first intermediate container and a second intermediate container: the low-temperature bath liquefies $CO_2$ and then puts the liquefied $CO_2$ into the $CO_2$ intermediate container, then the constant-speed and constant-pressure pump provides a displacement pressure, and sets a constant pressure or a constant displacement to drive the liquefied $CO_2$ out of the intermediate container, the liquefied $CO_2$ flows through the check valve and then is injected into an artificial wellbore, and an artificial fracture is formed at the uncased part of the wellbore in the core by building a pressure; similarly, the constant-speed and constant-pressure pump absorbs water from the first water storage tank and drives the water into an upper end of the intermediate container to provide the displacement pressure, the acid fluid, the fracturing fluid or the sand-carrying fluid at a lower end of the intermediate container is injected into the artificial wellbore, the artificial fracture is formed at the uncased part of the wellbore in the core, and a proppant is carried into the fracture to form an artificial propped fracture with a certain conductivity; and moreover, the lower ends of the two intermediate containers are both provided with a mixer, which is used for mixing a coloring agent, the proppant and the fracturing fluid evenly.

The stress sensitivity testing part is composed of the first water storage tank, the constant-speed and constant-pressure pump, the first intermediate container, the second intermediate container, as well as an electronic balance, a second water storage tank, an $N_2$ check valve, a flow controller, an $N_2$ pressure regulating valve, an $N_2$ gas cylinder, an X-axis seepage plate, a Z-axis seepage plate, a Y-axis seepage plate and a sealant rubber sheath: the seepage plates are fixed and sealed with the core through the sealant rubber sheath, so as to measure a gas permeability and a liquid permeability; and nitrogen with a constant volume flow is injected into the wellbore using the pressure regulating valve and the flow controller or a liquid in the intermediate container is injected into the wellbore using the constant-speed and constant-pressure pump, and the nitrogen or the liquid flows out from one or all of the X-axis, Y-axis and Z-axis seepage plates, or is injected into one of all of the X-axis, Y-axis and Z-axis seepage plates and flows out from the wellbore, so as to simulate flowing of the gas or the liquid from the wellbore to a reservoir, and flowing of the gas or the liquid from the reservoir to the wellbore.

Alternating injection of different operating fluids including the fracturing fluid, the liquid carbon dioxide or the acid fluid is able to be flexibly realized through conversion connection among five quick-release interfaces for fracturing stimulation, and injection of the gas and the liquid from the wellbore to the reservoir or from the reservoir to the wellbore is selected, thus greatly improving an experimental efficiency.

The fracture monitoring part is composed of a first computer, the electronic balance, the constant-speed and constant-pressure pump, the triaxial hydraulic pumps, the flow controller, as well as a second computer, an acoustic emission receiving device, acoustic emission probes and high-speed cameras with light sources: at most 16 acoustic emission probes are provided, front, rear, left and right surfaces may be respectively provided with four acoustic emission probes, the probes are connected with a signal amplifier and then collected to the acoustic emission receiving device, and then the probes are connected with the second computer; four high-speed cameras with the light sources are respectively located in the X-axis and Y-axis backing plates, and the cameras are connected with the second computer; and the second computer is responsible for monitoring fracture propagation in the core, and the first computer is responsible for controlling the constant speed and constant pressure pump, the triaxial hydraulic pumps, the mixers, the carbon dioxide liquefaction and the flow of the nitrogen, and monitoring and recording pressures in various parts of a pipeline, a quality of the balance, and the like.

Further, the constant-speed and constant-pressure pump is a double-cylinder pump, which may inject the liquid alternately and continuously, without having a condition that pressure building is unable to be maintained in a fracturing pipeline when a single-cylinder pump is unloaded, thus ensuring smooth fracturing, with a maximum displacement of 300 mL/min and a maximum pump pressure of 100 MPa, and the constant-speed and constant-pressure pump is provided with a pressure release valve, and may automatically release a pressure after the pressure exceeds a rated pump pressure.

Further, when the device is needed to simulate acidification or acid fracturing of the core, a part directly contacted with the acid fluid, such as the intermediate container, the valve, an on-way pipeline and the like, is made of an acid-resistant material, which is Hastelloy, a metal with an acid-resistant coating (such as polytetrafluoroethylene, polyphenylene sulfide and the like), or the like.

Further, the $CO_2$ intermediate container has a volume of 5 L, the low-temperature bath has a volume of 5 L, the liquefied $CO_2$ may be injected into the $CO_2$ intermediate container through the low-temperature bath, the two liquid intermediate containers both have a volume of 8 L, the first and second water storage tanks both have a volume of 10 L, and the hydraulic oil tank has a volume of 10 L.

Further, a maximum size of the core suitable for the device is 50 cm×50 cm×50 cm, and the core with a smaller size, such as 30 cm×30 cm×30 cm, 10 cm×10 cm×10 cm and the like, may be suitable for the device by adjusting sizes of the backing plates.

Further, a maximum uniaxial pressure that the device may apply in any direction of X, Y and Z is 35 MPa (50 cm$^3$), 70 MPa (30 cm$^3$) and 80 MPa (10 cm$^3$).

Further, a maximum number of channels in an acoustic emission system is 16, the four surfaces except upper and lower surfaces may be respectively provided with four probes, and an interpretation image has a geometric accuracy error no more than 1 cm.

Further, the sealant rubber sheath is made of high-quality rubber with a thickness not less than 3 cm, and sizes of the wellbore casing, the sealant rubber sheath and the seepage plates may be correspondingly adjusted according to the size of the core.

Further, the device may supply the gas to the core through the artificial wellbore or the X-axis, Y-axis and Z-axis seepage plates, thus simulating the flowing of the gas from the wellbore to the reservoir or from the reservoir to the wellbore, and the gas permeability of any single axis of the X, Y and Z axes is calculated through a volume flow of the gas, the size of the core and differential pressures at the inlet and outlet ends, with a calculation formula as follows (Hongjun Tang, Petrophysics, Petroleum Industry Press, 2014):

$$K_{g,d1} = \frac{2Q_g p_1 \mu_g D}{A(p_1^2 - p_2^2)} = \frac{Q_g p_1 \mu_g (L - 2r_w)}{L^2(p_1^2 - p_2^2)},$$

$$D = \frac{L}{2} - r_w, A = L^2.$$

Further, the device may supply the liquid to the core through the artificial wellbore or the X-axis, Y-axis and Z-axis seepage plates, thus simulating the flowing of the liquid from the wellbore to the reservoir or from the reservoir to the wellbore, and the liquid permeability of any single axis of the X, Y and Z axes is calculated through a mass flow of the liquid, the size of the core and the differential pressures at the inlet and outlet ends, with a calculation formula as follows:

$$K_{l,d1} = \frac{Q_l \mu_l D}{A(p_1 - p_2)} = \frac{Q_l \mu_l \left(\frac{L}{2} - r_w\right)}{L^2(p_1 - p_2)},$$

$$D = \frac{L}{2} - r_w, A = L^2.$$

Further, when the overall triaxial permeability of the core is measured, the X-axis, Y-axis and Z-axis seepage plates are opened at the same time, thus simulating the flowing of the gas in the reservoir to the wellbore, the flowing of the liquid in the reservoir to the wellbore, the flowing of the gas in the wellbore to the reservoir, and the flowing of liquid in the wellbore to the reservoir, so as to acquire the overall triaxial permeabilities in gas and liquid tests, with calculation formulas as follows:

$$K_{g,d3} = \frac{Q_g p_1 \mu_g \ln(r_e/r_w)}{\pi h(p_1^2 - p_2^2)} = \frac{Q_g p_1 \mu_g \ln(L - 2r_w)}{\pi L(p_1^2 - p_2^2)},$$

-continued $$K_{l,d3} = \frac{Q_l \mu_l \ln(r_e/r_w)}{2\pi h(p_1 - p_2)} = \frac{Q_l \mu_l \ln(L - 2r_w)}{\pi L(p_1 - p_2)},$$

$$h = L, r_e = \frac{L}{2}.$$

Wherein, $K_{g,d1}$ is a uniaxial gas permeability, $\mu m^2$; D is a length of the core, cm; A is a cross-sectional area of the core, cm$^2$; $Q_g$ is a set flow of the gas, mL/s; $p_1$ is a pressure at an injection end, $10^{-1}$ MPa; $\mu_g$ is a viscosity of the gas, mPa·s; L is a side length of the core, cm; h is a height of the core, cm; $r_e$ is a supply radius, cm; $r_w$ is a radius of the artificial wellbore, cm; $p_2$ is a pressure at a discharge end, $10^{-1}$ MPa; $K_{l,d1}$ is a uniaxial liquid permeability, $\mu m^2$; $Q_l$ is a flow of the liquid at the discharge end, mL/s; $\mu_l$ is a viscosity of the liquid, mPa·s; $K_{g,d3}$ is a triaxial gas permeability, $\mu m^2$; and $K_{l,d3}$ is a triaxial liquid permeability, $\mu m^2$.

A method for evaluating fracture initiation and propagation, and a stress sensitivity of a propped fracture using the above device sequentially includes the following steps:

step 1: setting X-axis, Y-axis and Z-axis pressures, and applying triaxial loads to the core;

step 2: testing a permeability of the core before fracturing with clean water or nitrogen, and calculating a uniaxial permeability or an overall triaxial permeability of the core flowing from the wellbore to a reservoir or from the reservoir to the wellbore;

step 3: preparing a required fracturing fluid and taking a proppant, adding the fracturing fluid into the first intermediate container as a prepad fluid, adding the fracturing fluid and the proppant into the second intermediate container and using the mixture as a sand-carrying fluid, and stirring the sand-carrying fluid evenly;

step 4: setting a constant displacement to inject the prepad fluid into the core, determining fracture initiation and propagation in the core through a shooting image, the acoustic emission signal and a pressure at an inlet of the wellbore, injecting the sand-carrying fluid into the core after the core is fractured (if the first intermediate container still has sufficient fracturing fluid, the fracturing fluid may be used as a displacement fluid to squeeze the remaining sand-carrying fluid in the pipeline into the fracture), and unloading a pressure of the fracturing pipeline after fracturing; or fracturing the core with liquid carbon dioxide; and step 5: testing a stress sensitivity of a propped fracture of the core after fracturing with clean water or nitrogen, setting the constant displacement to inject water or gas into the wellbore or the triaxial seepage plates, monitoring a quality of the electronic balance and changes of pressure gauges at the inlet and outlet ends to determine whether stable seepage is realized, and calculating the uniaxial permeability or the overall triaxial permeability of the core flowing from the wellbore to the reservoir or from the reservoir to the wellbore; and testing a change of a permeability of the propped fracture under different confining pressures by adjusting the triaxial pressures to evaluate the stress sensitivity of the propped fracture.

After the test, the core is split to observe the fracture propagation and placement of the proppant in the fracture, so that an acoustic emission interpretation image and a shooting image are verified.

Compared with the prior art, the present invention has the following beneficial effects:

(1) the present invention may realize fracturing with the fracturing fluid, fracturing with the liquid carbon dioxide, fracturing with the sand-carrying fluid or acid fracturing, and simulate different pumping processes of the prepad fluid, the sand-carrying fluid, the displacement fluid and the like through the constant-speed and constant-pressure pump, a carbon dioxide liquefying device and the intermediate containers with the mixers, while the triaxial hydraulic oil pumps simulate the three-dimensional crustal stresses borne by a rock in the reservoir;

(2) the present invention is provided with the acoustic emission device with 16 channels and 4 high-speed cameras with the light sources, and simultaneously monitors and records the fracture initiation and propagation in the core;

(3) the present invention solves a problem that a similar device is only able to simulate a single fracturing operation and lacks a fracturing effect evaluation method, evaluates the change of the permeability of the core before and after fracturing and the stress sensitivity of the propped fracture formed after the proppant enters the core under different confining pressures through gas and liquid test methods, and may simulate seepage processes including the flowing of the gas in the reservoir to the wellbore, the flowing of the liquid in the reservoir to the wellbore, the flowing of the gas in the wellbore to the reservoir and the flowing of the liquid in the wellbore to the reservoir;

(4) the present invention solves a series of problems in the current fracture stress sensitivity test, such as that the core and the fracture have excessively small sizes, the artificially split fracture and the manually added proppant do not conform to a fracturing reality, confining pressure loading does not conform to the three-dimensional crustal stresses, only one-way seepage is able to be simulated, and a seepage mode of the wellbore is unable to be simulated, thus improving the method for testing the stress sensitivity of the propped fracture which is hydraulically fractured; and (5) the present invention is able to simulate an integrated operation of two processes including the hydraulic fracturing with different fracturing fluids and the stress sensitivity test to the propped fracture, combines the fracture initiation and propagation with fracturing effect evaluation, and provides corresponding technical guidance for hydraulic fracturing mechanism study, construction parameter optimization and the fracturing effect evaluation.

Reference numerals: 1 refers to $CO_2$ check valve, 2 refers to $CO_2$ intermediate container, 3 refers to low-temperature bath, 4 refers to $CO_2$ pressure regulating valve, 5 refers to $CO_2$ gas cylinder, 6 refers to constant-speed and constant-pressure pump, 7 refers to first water storage tank, 8 refers to first intermediate container, 9 refers to second intermediate container, 10 refers to first computer, 11 refers to electronic balance, 12 refers to second water storage tank, 13 refers to $N_2$ check valve, 14 refers to flow controller, 15 refers to $N_2$ pressure regulating valve, 16 refers to $N_2$ gas cylinder, 17 refers to acoustic emission receiving device, 18 refers to Z-axis hydraulic pump, 19 refers to Y-axis hydraulic pump, 20 refers to X-axis hydraulic pump, 21 refers to oil tank, 22 refers to second computer, 23 refers to confining pressure cover plate, 24 refers to wellbore casing, 25 refers to wellbore sealant, 26 refers to high-speed cameras with light sources, 27 refers to uncased wellbore, 28 refers to X-axis seepage plate, 29 refers to Z-axis seepage plate, 30 refers to confining pressure base, 31 refers to Z-axis lower backing plate, 32 refers to Z-axis oil cylinder, 33 refers to Z-axis upper backing plate, 34 refers to X-axis backing plate, 35 refers to acoustic emission probes, 36 refers to sealant rubber sheath, 37 refers to X-axis oil cylinder, 38 refers to core supporting plate, 39 refers to Y-axis backing plate, 40 refers to Y-axis seepage plate, 41 refers to Y-axis oil cylinder, 42 refers to core, and A, B, C, D and E refer to quick-release interfaces.

DETAILED DESCRIPTION OF THE PREFERRED EMBODIMENTS

The present invention is further described hereinafter with reference to the accompanying drawings and the embodiments, so that those skilled in the art may understand the present invention. However, it shall be clear that the present invention is not limited to the scope of specific embodiments, and for those of ordinary skills in the art, various changes within the spirit and scope of the present invention defined and determined by the attached claims shall fall into the scope of protection.

Refer to FIG. 1 to FIG. 4.

A device for evaluating fracture initiation and propagation, and a stress sensitivity of a propped fracture includes a core part, a confining pressure loading part, a fracturing fluid pumping part, a stress sensitivity testing part and a fracture monitoring part.

Figure 4:
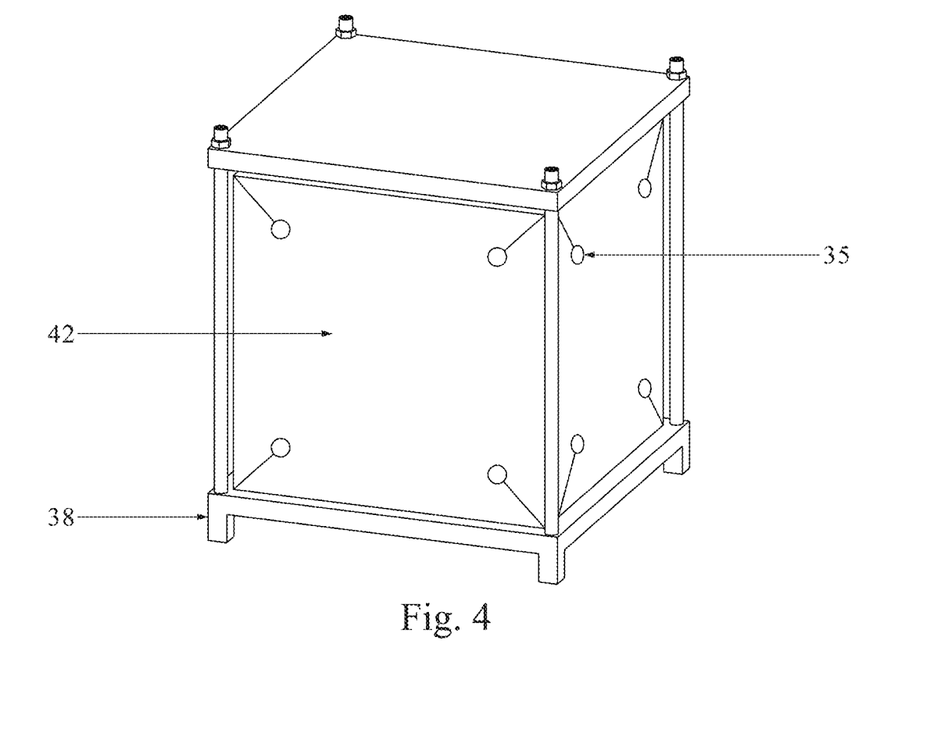
FIG. 4 is a structure diagram of a core part.

The core part includes a core 42, a wellbore casing 24, an uncased wellbore 27 and a core supporting plate 38. The core is located on the core supporting plate, at most 16 acoustic emission probes 35 are installed in the core, a borehole is arranged in a middle of the core, the wellbore casing (the wellbore casing is fixed in the borehole of the core through a wellbore sealant 25) is arranged at an upper end of the borehole, and the uncased wellbore is arranged at a lower end of the borehole.

Figure 2:
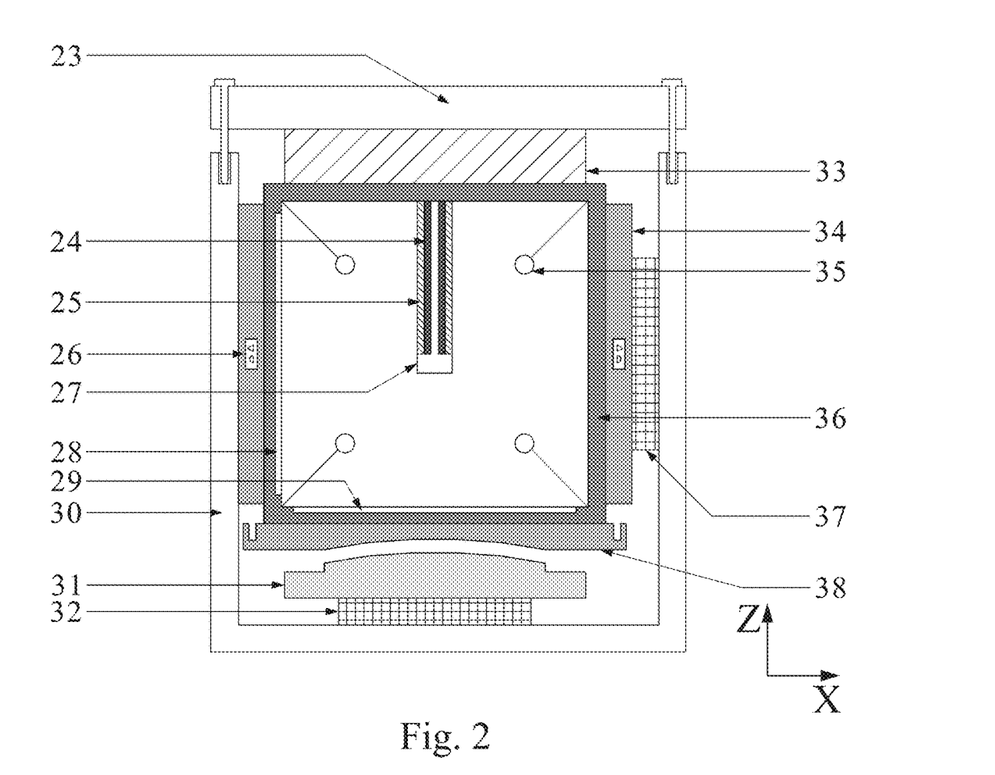
FIG. 2 is a structure diagram of an X-Z cross-section of a confining pressure base.
Figure 3:
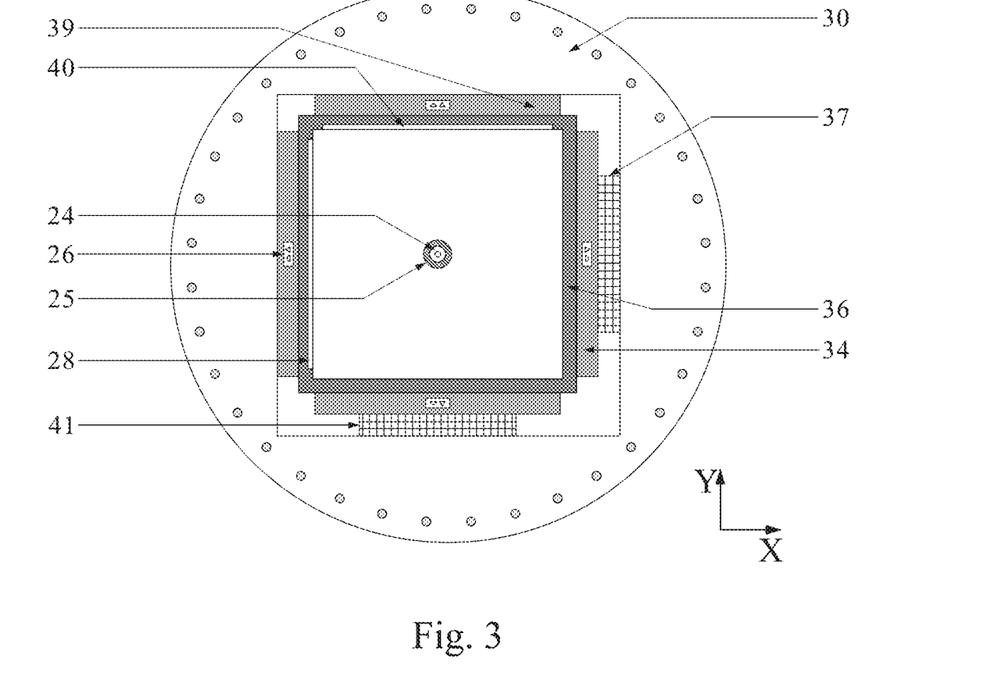
FIG. 3 is a structure diagram of an X-Y cross-section of the confining pressure base.

The confining pressure loading part includes triaxial hydraulic pumps, an oil tank 21, a confining pressure cover plate 23 and a confining pressure base 30. Inlet ends of the triaxial hydraulic pumps are connected with the oil tank 21 and outlet ends of the triaxial hydraulic pumps are respectively connected with triaxial oil cylinders, and pressure gages and pressure release valves are arranged at the outlet ends for displaying and unloading pressures. The core part is located in a space formed by the confining pressure cover plate 23 and the confining pressure base 30, and the oil cylinders, backing plates, seepage plates and the core are respectively arranged in the space from outside to inside. The seepage plates are fixed and sealed with the core through a sealant rubber sheath 36, and the triaxial hydraulic pumps apply triaxial confining pressures to the core through the oil cylinders, the backing plates and the seepage plates in X, Y and Z directions respectively.

The triaxial hydraulic pumps include an X-axis hydraulic pump 20, a Y-axis hydraulic pump 19 and a Z-axis hydraulic pump 18, and the triaxial oil cylinders include an X-axis oil cylinder 37, a Y-axis oil cylinder 41 and a Z-axis oil cylinder 32. The triaxial confining pressures are applied to the core by the X-axis hydraulic pump through the X-axis oil cylinder 37, the X-axis backing plate 34 and the X-axis seepage plate 28, by the Y-axis hydraulic pump through the Y-axis oil cylinder 41, the Y-axis backing plate 39 and the Y-axis seepage plate 40, and by the Z-axis hydraulic pump through the Z-axis oil cylinder 32, a Z-axis upper backing plate 33 or a Z-axis lower backing plate 31, and the Z-axis seepage plate 29.

Figure 1:
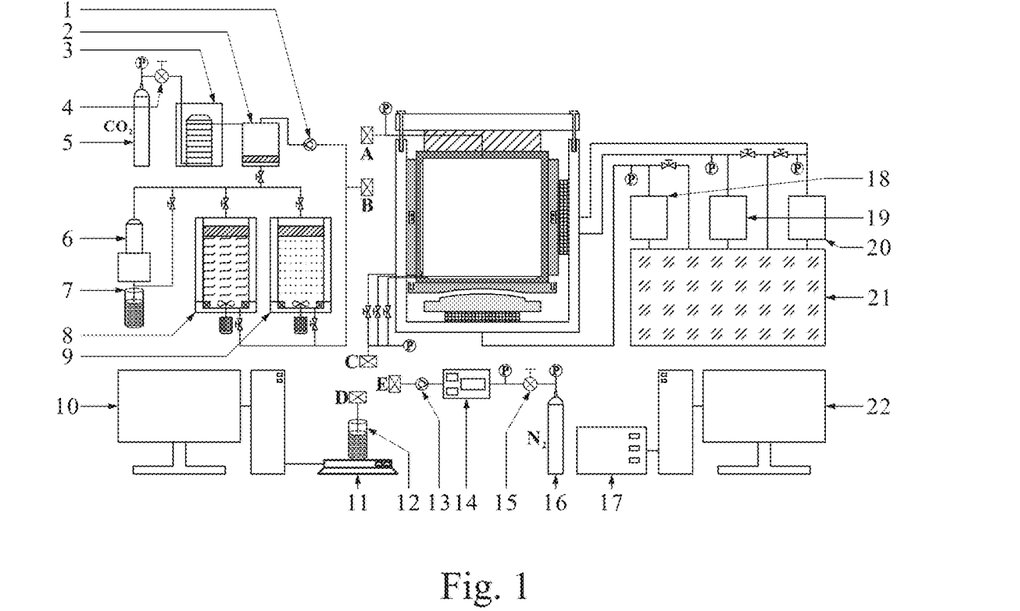
FIG. 1 is a structure diagram of a device for evaluating fracture initiation and propagation, and a stress sensitivity of a propped fracture.

The fracturing fluid pumping part includes a $CO_2$ check valve 1, a $CO_2$ intermediate container 2, a low-temperature bath 3, a $CO_2$ pressure regulating valve 4, a $CO_2$ gas cylinder 5, a constant-speed and constant-pressure pump 6, a first water storage tank 7, a first intermediate container 8 and a second intermediate container 9. The low-temperature bath liquefies $CO_2$ and then discharges the liquefied $CO_2$ into the $CO_2$ intermediate container, the constant-speed and constant-pressure pump provides a displacement pressure to drive the liquefied $CO_2$ out of the intermediate container, the liquefied $CO_2$ flows through the $CO_2$ check valve and then is injected into the core, and facture initiation at an uncased part forms an artificial fracture. Alternatively, the constant-speed and constant-pressure pump absorbs water from the first water storage tank and provides the displacement pressure, the prepad fluid in the first intermediate container and the sand-carrying fluid in the second intermediate container are injected into the core, the facture initiation at the uncased part forms the artificial fracture, and the proppant is carried into the fracture to prop the fracture.

The stress sensitivity testing part includes the constant-speed constant-pressure pump 6, the first water storage tank 7, the first intermediate container 8, the second intermediate container 9, as well as an electronic balance 11, a second water storage tank 12, an $N_2$ check valve 13, a flow controller 14, an $N_2$ pressure regulating valve 15, an $N_2$ gas cylinder 16, an X-axis seepage plate 28, a Y-axis seepage plate 40 and a Z-axis seepage plate 29. The X-axis seepage plate 28, the Y-axis seepage plate 40 and the Z-axis seepage plate 29 are located in three directions of the core, and the seepage plates are fixed and sealed with the core through the sealant rubber sheath 36, so as to measure a gas permeability and a liquid permeability of the core.

Nitrogen with a constant volume flow is injected into the uncased wellbore through the $N_2$ check valve using the $N_2$ pressure regulating valve and the flow controller, and the gas flows out from the X-axis, Y-axis and Z-axis seepage plates, or is injected into the X-axis, Y-axis and Z-axis seepage plates and flows out from the wellbore. The liquid in the first intermediate container or the second intermediate container is injected into the wellbore using the constant-speed and constant-pressure pump and flows out from the X-axis, Y-axis and Z-axis seepage plates, or is injected into the X-axis, Y-axis and Z-axis seepage plates and flows out from the wellbore, so as to evaluate a sensitivity of a permeability of a proppant-filled fracture of the core after fracturing changed with triaxial stresses, and a change of the permeability of the proppant-filled fracture of the core before and after fracturing.

The fracture monitoring part includes a first computer 10, the electronic balance 11, the constant-speed and constant-pressure pump 6, the triaxial hydraulic pumps, the flow controller 14, as well as a second computer 22, an acoustic emission receiving device 17, the acoustic emission probes 35 and high-speed cameras 26 with light sources. The first computer is connected with the electronic balance, the constant-speed and constant-pressure pump, the triaxial hydraulic pumps and the flow controller, and is used for collecting and recording pressure data and flow data. The second computer is connected with the acoustic emission receiving device and the high-speed cameras with the light sources, the acoustic emission receiving device receives signals transmitted by the acoustic emission probes, and the high-speed cameras with the light sources are respectively located in an X-axis backing plate and a Y-axis backing plate. The second computer monitors and analyzes fracture initiation and propagation of a hydraulic fracture in the core and an acoustic emission signal through the acoustic emission receiving device and the high-speed cameras with the light sources.

It should be pointed out that, when it is necessary to simulate flowing from a reservoir to the wellbore, an injection end is a quick-release interface C and a discharge end is a quick-release interface A, and when it is necessary to simulate flowing from the wellbore to the reservoir, the injection end is the quick-release interface A and the discharge end is the quick-release interface C. When a liquid or the liquid carbon dioxide is injected, the injection end is connected with a quick-release interface B, and when the nitrogen or another gas is injected, the injection end is connected with a quick-release interface E. When it is necessary to calculate a flow of the liquid at the discharge end, the discharge end is connected with a quick-release interface D, while the discharge end of the gas does not need to be connected with any interface.

Embodiment 1

The device is used for evaluating fracturing on an outcrop core of 50 cm×50 cm×50 cm, and a stress sensitivity of a propped fracture, and specific operation steps are as follows.

In step 1, a borehole with a diameter of 2 cm and a depth of 30 cm is drilled at a top of a natural core, then the wellbore casing is fixed in the borehole with glue, and holes required for installing the acoustic emission probes are drilled in four surfaces of the core. The 16 acoustic emission probes, the seepage plates and the sealant rubber sheath are sequentially installed, and an edge of the rubber sheath is sealed and reinforced with the glue.

In step 2, the core is put into the confining pressure base through the device shown in FIG. 4, then the Z-axis upper backing plate and the confining pressure cover plate are installed and a bolt is tightened, and a wellbore pipeline, a fracturing fluid injection pipeline, a seepage pipeline, an acoustic emission data line and a camera data line are connected.

In step 3, an X-axis pressure is set as 20 MPa, a Y-axis pressure is set as 25 MPa, and a Z-axis pressure is set as 30 MPa, and triaxial loads are applied to the core to simulate three-dimensional crustal stresses of a stratum, which is maintained for more than 30 minutes after reaching a specified pressure.

In step 4, when a permeability of the core before fracturing is tested with clean water, the quick-release interfaces B-C and A-D are connected, 6 L of clean water is filled into the first intermediate container, three constant displacements of 50 mL/min, 100 mL/min and 150 mL/min are respectively set to inject water into the triaxial seepage plates, and a quality of the electronic balance and changes of pressure gauges at the injection end and a wellbore end are monitored to determine whether stable seepage is realized. A volume flow, a size of the core, a radius of the wellbore and a pressure are acquired through a mass flow of the electronic balance, and an overall triaxial permeability of the core in the case of the flowing from the reservoir to the wellbore is calculated according to the following formula:

$$K_{1,d3} = \frac{Q_1 \mu_1 \ln(L/2r_w)}{2\pi L(p_1 - p_2)}.$$

In step 5, 12 L of guanidine gum fracturing fluid is prepared, and 1200 g of 40/60-mesh ceramsite proppant is taken. 6 L of fracturing fluid is added into the first intermediate container as a prepad fluid for fracturing, and 6 L of fracturing fluid and the proppant are added into the second intermediate container as a sand-carrying fluid for propping a fracture. The fracturing fluids are both added with a coloring agent, and mixers are opened to stirred the mixtures evenly.

In step 6, the quick-release interfaces A-B and C-D are connected, the constant displacement of 100 mL/min is set to inject the prepad fluid into the wellbore, and fracture initiation and propagation in the core are determined through a shooting image, an acoustic emission interpretation image and a pressure at an inlet of the wellbore. The constant displacement of 60 mL/min is set to inject the sand-carrying fluid into the wellbore after the core is fractured, if the first intermediate container still has sufficient fracturing fluid, the fracturing fluid may be used as a displacement fluid to squeeze the remaining sand-carrying fluid in the pipeline into the fracture, and a pressure of the fracturing pipeline is unloaded after fracturing.

In step 7, when the stress sensitivity of the propped fracture of the core after fracturing is tested with clean water, the quick-release interfaces B-C and A-D are connected, 6 L of clear water is filled into the first intermediate container, three constant displacements of 50 mL/min, 100 mL/min and 150 mL/min are respectively set to inject water into the triaxial seepage plates, and the quality of the electronic balance, the changes of the pressure gauges at the injection end and the wellbore end are monitored to determine whether the stable seepage is realized. The volume flow, the size of the core, the radius of the wellbore and the pressure are acquired through the mass flow of the electronic balance, and the overall triaxial permeability of the core in the case of the flowing from the reservoir to the wellbore is calculated according to the formula. X-axis, Y-axis and Z-axis pressures are sequentially adjusted as 18 MPa-23 MPa-30 MPa, 16 MPa-21 MPa-30 MPa and 26 MPa-28 MPa-30 MPa, and a change of the permeability of the propped fracture under different confining pressures is tested to evaluate the stress sensitivity of the propped fracture.

In step 8, after corresponding test is completed, the pressure of the pipeline and the triaxial pressures are unloaded, the core is split to observe the fracture propagation and placement of the proppant in the fracture, so that the acoustic emission interpretation image, the shooting image and the like are verified, and then the device is cleaned up and the test is ended.

A change of the overall triaxial permeability in the case of flowing of the liquid in the core to the wellbore acquired through the above test is shown in Table 1.

TABLE 1

Stress Sensitivity Test Result of Overall Triaxial Permeability of Propped Fracture of Core

| Pressurization condition of X-Y-X core axis of core/MPa | Overall triaxial permeability in liquid test ($\times 10^{-3}$ μm$^2$) |
|---|---|
| Before fracturing 20-25-30 | 3.15 |
| After fracturing 20-25-30 | 27.64 |
| After fracturing 18-23-30 | 28.59 |
| After fracturing 16-21-30 | 29.37 |
| After fracturing 26-28-30 | 22.06 |

Figure 5:
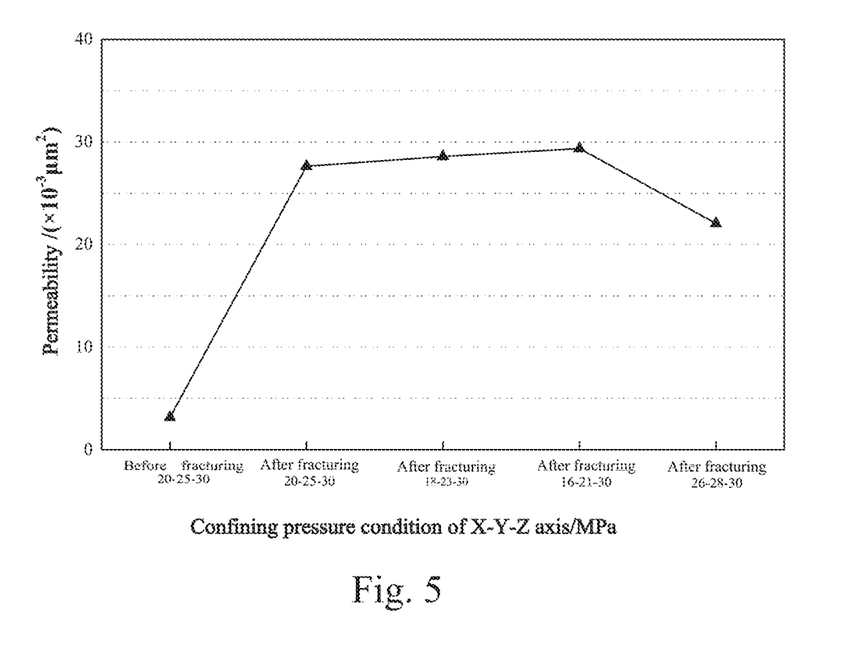
FIG. 5 is a curve of a stress sensitivity of a permeability of a propped fracture of a core in an embodiment.

The above test data is drawn into a curve as shown in FIG. 5. An initial permeability of the core is only $3.15 \times 10^{-3}$ μm$^2$, the propped fracture is produced in the core through sand fracturing, then the permeability of the core is increased to $27.64 \times 10^{-3}$ μm$^2$ and increased slightly with gradual decreases of the X-axis and Y-axis confining pressures, which indicates that the propped fracture has an opening tendency during the decreases of the confining pressures. However, when the X-axis and Y-axis confining pressures are increased, the permeability of the core is decreased to $22.06 \times 10^{-3}$ μm$^2$, which is lower than the initial permeability after fracturing, which indicates that the propped fracture has a closing tendency during the increases of the confining pressures, which means that the permeability of the propped fracture of the core has obvious stress sensitivity.

It should be pointed out that all tests performed in the embodiment, including the other three confining pressures performed before fracturing, after fracturing and after fracturing, simulate the flowing of the liquid in the reservoir to the wellbore, and the three displacements of 50 mL/min, 100 mL/min and 150 mL/min are used in all tests. After flow data and pressure data at one displacement are stable, the other displacements are used to calculate the permeabilities at the three displacements. Finally, an average value of the three permeabilities is taken as the permeability under certain confining pressure condition to evaluate the stress sensitivity of the propped fracture of the core.

The foregoing is not intended to limit the present invention in any form. Although the present invention has been disclosed in the above embodiments, the embodiments are not intended to limit the present invention. Those skilled in the art may make appropriate changes or modifications according to the technical contents disclosed above to form equivalent embodiments with equivalent changes without departing from the scope of the technical solutions of the present invention. However, any simple amendments, equivalent changes and modifications made to the above embodiments according to the technical essence of the present invention without departing from the contents of the technical solutions of the present invention still fall into the scope of the present invention.

What is claimed is:

1. A device for evaluating fracture initiation and propagation, and a stress sensitivity of a propped fracture, comprising a core part, a confining pressure loading part, a fracturing fluid pumping part, a stress sensitivity testing part and a fracture monitoring part, wherein the core part comprises a core (42), a wellbore casing (24), an uncased wellbore (27) and a core supporting plate (38), the core is located on the core supporting plate, at most 16 acoustic emission probes (35) are installed in the core, a borehole is arranged in a middle of the core, the wellbore casing is arranged at an upper end of the borehole, and the uncased wellbore is arranged at a lower end of the borehole;

wherein the confining pressure loading part comprises triaxial hydraulic pumps, an oil tank (21), a confining pressure cover plate (23) and a confining pressure base (30), inlet ends of the triaxial hydraulic pumps are connected with the oil tank (21) and outlet ends of the triaxial hydraulic pumps are respectively connected with triaxial oil cylinders, the core part is located in a space formed by the confining pressure cover plate and the confining pressure base, the oil cylinders, backing plates, seepage plates and the core are respectively arranged in the space from outside to inside, the seepage plates are fixed and sealed with the core through a sealant rubber sheath (36), and the triaxial hydraulic pumps apply triaxial confining pressures to the core through the oil cylinders, the backing plates and the seepage plates in X, Y and Z directions respectively;

wherein the fracturing fluid pumping part comprises a $CO_2$ check valve (1), a $CO_2$ intermediate container (2), a low-temperature bath (3), a $CO_2$ pressure regulating valve (4), a $CO_2$ gas cylinder (5), a constant-speed and constant-pressure pump (6), a first water storage tank (7), a first intermediate container (8) and a second intermediate container (9);

wherein the stress sensitivity testing part comprises the constant-speed and constant-pressure pump (6), the first water storage tank (7), the first intermediate container (8), the second intermediate container (9), as well as an electronic balance (11), a second water storage tank (12), an $N_2$ check valve (13), a flow controller (14), an $N_2$ pressure regulating valve (15), an $N_2$ gas cylinder (16), an X-axis seepage plate (28), a Y-axis seepage plate (40) and a Z-axis seepage plate (29), the X-axis seepage plate, the Y-axis seepage plate and the Z-axis seepage plate are located in three directions of the core, the seepage plates are fixed and sealed with the core through the sealant rubber sheath (36), so as to measure a gas permeability and a liquid permeability of the core; and wherein the fracture monitoring part comprises a first computer (10), the electronic balance (11), the constant-speed and constant-pressure pump (6), the triaxial hydraulic pumps, the flow controller (14), as well as a second computer (22), an acoustic emission receiving device (17), the acoustic emission probes (35) and high-speed cameras (26) with light sources, wherein the first computer is connected with the electronic balance, the constant-speed and constant-pressure pump, the triaxial hydraulic pumps and the flow controller, and is used for collecting and recording pressure data and flow data, wherein the second computer is connected with the acoustic emission receiving device and the high-speed cameras with the light sources, the acoustic emission receiving device receives signals transmitted by the acoustic emission probes, the high-speed cameras with the light sources are respectively located in an X-axis backing plate and a Y-axis backing plate, and the second computer monitors and analyzes fracture initiation and propagation of a hydraulic fracture in the core and an acoustic emission signal.

2. The device for evaluating the fracture initiation and propagation, and the stress sensitivity of the propped fracture according to claim 1, wherein the triaxial hydraulic pumps comprise an X-axis hydraulic pump (20), a Y-axis hydraulic pump (19) and a Z-axis hydraulic pump (18), and the triaxial oil cylinders comprise an X-axis oil cylinder (37), a Y-axis oil cylinder (41) and a Z-axis oil cylinder (32); and the triaxial confining pressures are applied to the core by the X-axis hydraulic pump through the X-axis oil cylinder (37), the X-axis backing plate (34) and the X-axis seepage plate (28), by the Y-axis hydraulic pump through the Y-axis oil cylinder (41), the Y-axis backing plate (39) and the Y-axis seepage plate (40), and by the Z-axis hydraulic pump through the Z-axis oil cylinder (32), a Z-axis upper backing plate (33) or a Z-axis lower backing plate (31), and the Z-axis seepage plate (29).

3. A method for evaluating fracture initiation and propagation, and a stress sensitivity of a propped fracture using the device according to claim 1, sequentially comprising the following steps:

step 1: setting X-axis, Y-axis and Z-axis pressures, and applying triaxial loads to the core;

step 2: testing a permeability of the core before fracturing with clean water or nitrogen, and calculating a uniaxial permeability or an overall triaxial permeability of the core flowing from the wellbore to a reservoir or from the reservoir to the wellbore;

step 3: preparing a required fracturing fluid and taking a proppant, adding the fracturing fluid into the first intermediate container as a prepad fluid, adding the fracturing fluid and the proppant into the second intermediate container and using the mixture as a sand-carrying fluid, and stirring the sand-carrying fluid evenly;

step 4: setting a constant displacement to inject the prepad fluid into the core, determining fracture initiation and propagation in the core through a shooting image, the acoustic emission signal and a pressure at an inlet of the wellbore, and injecting the sand-carrying fluid into the core after the core is fractured; or fracturing the core with liquid carbon dioxide; and step 5: testing a stress sensitivity of a propped fracture of the core after fracturing with clean water or nitrogen, setting the constant displacement to inject water or gas into the wellbore or the triaxial seepage plates, monitoring a quality of the electronic balance and changes of pressure gauges at the inlet and outlet ends, and calculating the uniaxial permeability or the overall triaxial permeability of the core flowing from the wellbore to the reservoir or from the reservoir to the wellbore; and testing a change of a permeability of the propped fracture under different confining pressures by adjusting the triaxial pressures to evaluate the stress sensitivity of the propped fracture.

4. The method according to claim 3, wherein the low-temperature bath liquefies $CO_2$ and then discharges the liquefied $CO_2$ into the $CO_2$ intermediate container, the constant-speed and constant-pressure pump provides a displacement pressure to drive the liquefied $CO_2$ out of the intermediate container, the liquefied $CO_2$ flows through the $CO_2$ check valve and then is injected into the core, and facture initiation at an uncased part forms an artificial fracture; or the constant-speed and constant-pressure pump absorbs water from the first water storage tank and provides the displacement pressure, the prepad fluid in the first intermediate container and the sand-carrying fluid in the second intermediate container are injected into the core, the facture initiation at the uncased part forms the artificial fracture, and the proppant is carried into the fracture to prop the fracture.

5. The method according to claim 3, wherein nitrogen with a constant volume flow is injected into the uncased wellbore through the $N_2$ check valve using the $N_2$ pressure regulating valve and the flow controller, and the gas flows out from the X-axis, Y-axis and Z-axis seepage plates, or is injected into the X-axis, Y-axis and Z-axis seepage plates and flows out from the wellbore; and the liquid in the first intermediate container or the second intermediate container is injected into the wellbore using the constant-speed and constant-pressure pump and flows out from the X-axis, Y-axis and Z-axis seepage plates, or is injected into the X-axis, Y-axis and Z-axis seepage plates and flows out from the wellbore, so as to evaluate a sensitivity of a permeability of a proppant-filled fracture of the core after fracturing changed with triaxial stresses, and a change of the permeability of the proppant-filled fracture of the core before and after fracturing.

6. A method for evaluating fracture initiation and propagation, and a stress sensitivity of a propped fracture using the device according to claim 2, sequentially comprising the following steps:

step 1: setting X-axis, Y-axis and Z-axis pressures, and applying triaxial loads to the core;

step 2: testing a permeability of the core before fracturing with clean water or nitrogen, and calculating a uniaxial permeability or an overall triaxial permeability of the core flowing from the wellbore to a reservoir or from the reservoir to the wellbore;

step 3: preparing a required fracturing fluid and taking a proppant, adding the fracturing fluid into the first intermediate container as a prepad fluid, adding the fracturing fluid and the proppant into the second intermediate container and using the mixture as a sand-carrying fluid, and stirring the sand-carrying fluid evenly;

step 4: setting a constant displacement to inject the prepad fluid into the core, determining fracture initiation and propagation in the core through a shooting image, the acoustic emission signal and a pressure at an inlet of the wellbore, and injecting the sand-carrying fluid into the core after the core is fractured; or fracturing the core with liquid carbon dioxide; and step 5: testing a stress sensitivity of a propped fracture of the core after fracturing with clean water or nitrogen, setting the constant displacement to inject water or gas into the wellbore or the triaxial seepage plates, monitoring a quality of the electronic balance and changes of pressure gauges at the inlet and outlet ends, and calculating the uniaxial permeability or the overall triaxial permeability of the core flowing from the wellbore to the reservoir or from the reservoir to the wellbore; and testing a change of a permeability of the propped fracture under different confining pressures by adjusting the triaxial pressures to evaluate the stress sensitivity of the propped fracture.

7. The method according to claim 6, wherein the low-temperature bath liquefies $CO_2$ and then discharges the liquefied $CO_2$ into the $CO_2$ intermediate container, the constant-speed and constant-pressure pump provides a displacement pressure to drive the liquefied $CO_2$ out of the intermediate container, the liquefied $CO_2$ flows through the $CO_2$ check valve and then is injected into the core, and facture initiation at an uncased part forms an artificial fracture; or the constant-speed and constant-pressure pump absorbs water from the first water storage tank and provides the displacement pressure, the prepad fluid in the first intermediate container and the sand-carrying fluid in the second intermediate container are injected into the core, the facture initiation at the uncased part forms the artificial fracture, and the proppant is carried into the fracture to prop the fracture.

8. The method according to claim 6, wherein nitrogen with a constant volume flow is injected into the uncased wellbore through the $N_2$ check valve using the $N_2$ pressure regulating valve and the flow controller, and the gas flows out from the X-axis, Y-axis and Z-axis seepage plates, or is injected into the X-axis, Y-axis and Z-axis seepage plates and flows out from the wellbore; and the liquid in the first intermediate container or the second intermediate container is injected into the wellbore using the constant-speed and constant-pressure pump and flows out from the X-axis, Y-axis and Z-axis seepage plates, or is injected into the X-axis, Y-axis and Z-axis seepage plates and flows out from the wellbore, so as to evaluate a sensitivity of a permeability of a proppant-filled fracture of the core after fracturing changed with triaxial stresses, and a change of the permeability of the proppant-filled fracture of the core before and after fracturing.

* * * * *